United States Patent
Saito et al.

(10) Patent No.: US 9,212,991 B2
(45) Date of Patent: Dec. 15, 2015

(54) REFRACTIVE INDEX MEASURMENT APPARATUS AND REFRACTIVE INDEX MEASURMENT METHOD

(75) Inventors: Yuka Saito, Saitama (JP); Nobuyuki Hashimoto, Saitama (JP)

(73) Assignee: CITIZEN HOLDINGS CO., LTD., Tokyo (JP)

( * ) Notice: Subject to any disclaimer, the term of this patent is extended or adjusted under 35 U.S.C. 154(b) by 130 days.

(21) Appl. No.: 13/817,439

(22) PCT Filed: Aug. 4, 2011

(86) PCT No.: PCT/JP2011/068336
§ 371 (c)(1),
(2), (4) Date: Feb. 16, 2013

(87) PCT Pub. No.: WO2012/023481

PCT Pub. Date: Feb. 23, 2012

(65) Prior Publication Data
US 2013/0155394 A1 Jun. 20, 2013

(30) Foreign Application Priority Data

Aug. 19, 2010 (JP) .................... 2010-183973

(51) Int. Cl.
*G01N 21/41* (2006.01)
*G01N 21/03* (2006.01)

(52) U.S. Cl.
CPC .............. *G01N 21/41* (2013.01); *G01N 21/03* (2013.01)

(58) Field of Classification Search
CPC .......... G01N 21/41; G02B 13/18; G02B 5/18; G02B 27/22; G02B 27/44; G11B 7/00; G03H 1/08; H01L 21/00; H01L 33/00

USPC .............. 356/128; 359/719, 566, 571
See application file for complete search history.

(56) References Cited

U.S. PATENT DOCUMENTS

| 4,436,420 A | 3/1984 | Depp et al. |
| 2003/0059725 A1* | 3/2003 | Takahashi et al. ............ 430/321 |

(Continued)

FOREIGN PATENT DOCUMENTS

| CN | 101116026 A | 1/2008 |
| JP | H05-072126 A | 3/1993 |

(Continued)

OTHER PUBLICATIONS

International Search Report for PCT/JP2011/068336, Nov. 1, 2011.

(Continued)

*Primary Examiner* — Tarifur Chowdhury
*Assistant Examiner* — Isiaka Akanbi

(57) ABSTRACT

A refractive index measurement apparatus includes a light source, a measurement cell including a sample as an object of refractive index measurement and diffracting light incident from the light source, a detector that detects the amount of diffracted light in at least one diffraction order other than zero order of diffracted light exiting from the measurement cell, and a control unit that determines refractive index of the sample based on the measured value of the amount of diffracted light by the detector. The measurement cell includes two substrates disposed so as to be opposed to each other and a diffraction grating disposed between the two substrates, and the diffraction grating has a plurality of members whose width decreases stepwise as approaching from one of the substrates to the other of the substrates, the sample being filled in the space between the substrates not occupied by the diffraction grating.

4 Claims, 5 Drawing Sheets

(56) References Cited

U.S. PATENT DOCUMENTS

2004/0256628 A1* 12/2004 Chin et al. .................. 257/98
2007/0258345 A1* 11/2007 Yamada et al. .......... 369/112.05
2008/0030632 A1   2/2008 Murata
2008/0049328 A1*  2/2008 Zhou ........................... 359/566

FOREIGN PATENT DOCUMENTS

| JP | 2002-168780 A | 6/2002 |
| JP | 2005-098743 A | 4/2005 |
| JP | 2005-181150 A | 7/2005 |
| JP | 2006-170727 A | 6/2006 |
| JP | 2007-292509 A | 11/2007 |

OTHER PUBLICATIONS

The State Intellectual Property Office of the People's Republic of China (SIPO), Office Action for Chinese Patent Application No. 201180040192.3, Sep. 2, 2014.

The State Intellectual Property of the People's Republic of China (SIPO), Office Action for Chinese Patent Application No. 201180040192.3, Apr. 27, 2015.

* cited by examiner

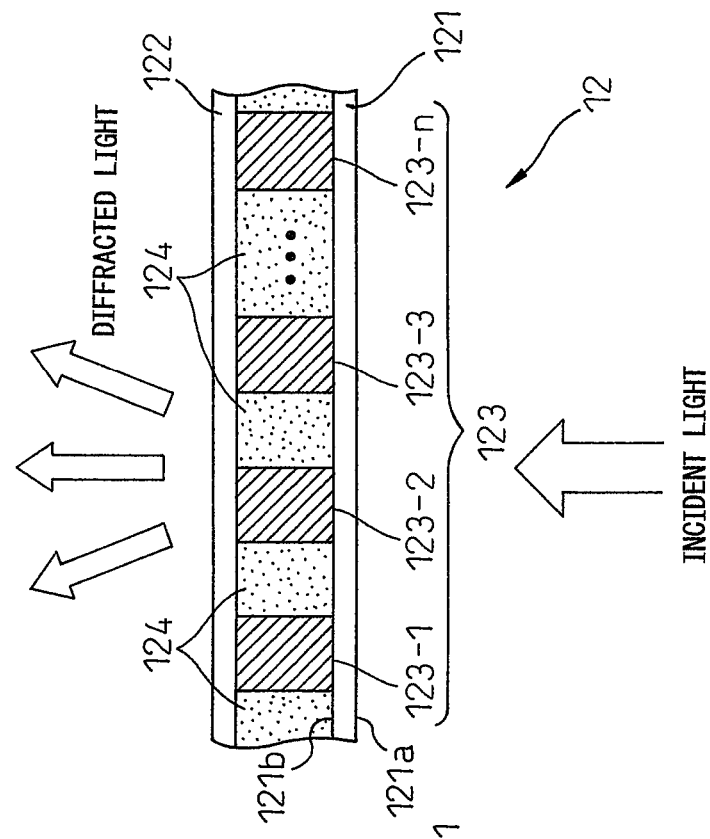
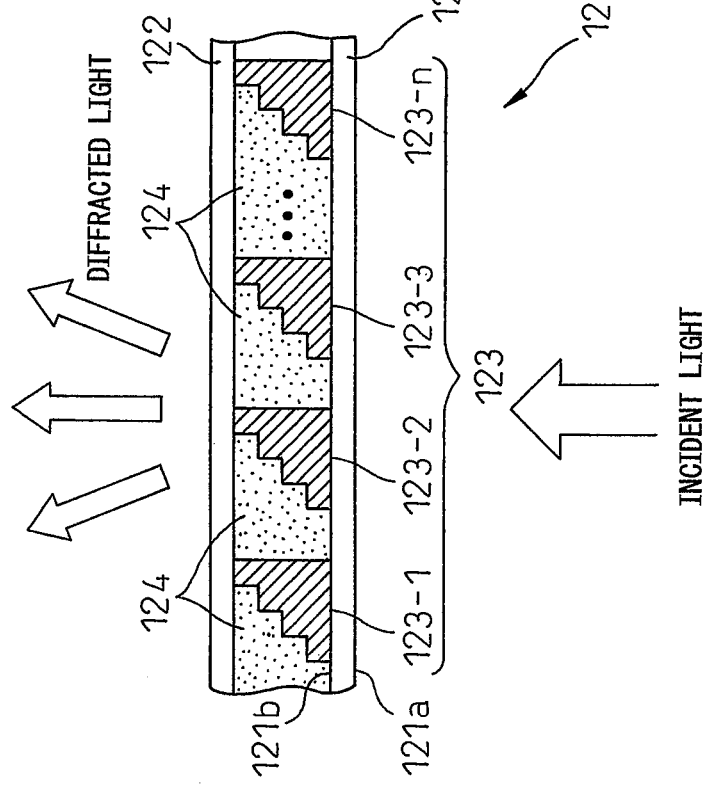

REFRACTIVE INDEX MEASURMENT APPARATUS AND REFRACTIVE INDEX MEASURMENT METHOD

FIELD OF THE INVENTION

The present invention relates to a refractive index measurement apparatus and a refractive index measurement method for measuring refractive index of a sample.

BACKGROUND ART

Various apparatuses and methods have been proposed in prior art for measuring refractive index of a sample such as gases, liquids, etc. As one representative apparatuse for measuring refractive index, an Abbe's refractometer has been known which measures refractive index by using a prism for studying critical angle of total reflection of a sample.

A refractive index measurement apparatus using interference of light has also been proposed (see, for example, Japanese Unexamined Patent Application Publication No. 2002-168780).

Further, a refraction index measurement method using diffraction of light has also been proposed. As one such measurement method, Japanese Unexamined Patent Application Publication No. 2006-170727 discloses an evaluation method for evaluating a polarized beam splitter to measure refractive index modulation quantity of a polarized beam splitter as a diffraction device in which a composition comprising a non-polymerizable liquid crystal, a polymerizable monomer and a photo-polymerization initiator is exposed to light by a two-beam interference exposure method in order to form a periodic structure consisting of a region exhibiting optical anisotropy and a region exhibiting optical isotropy.

In this method, while temperature of the polarized beam splitter is controlled, the polarized beam splitter is irradiated with a laser beam to measure diffraction efficiency, and from the relationship between refractive index modulation quantity and the diffraction efficiency, and by using temperature characteristics of the diffraction efficiency, the refraction index modulation quantity corresponding to the diffraction efficiency is identified.

Further, Japanese Unexamined Patent Application Publication No. 2007-292509 discloses a refractive index measurement method in which refraction index of a sample covering a diffraction device is determined by measuring zero order diffraction efficiency of a diffraction device, and identifying the refractive index as one that best matches the measured zero order diffraction efficiency and the theoretical diffraction efficiency calculated by using the grating shape of the diffraction device.

SUMMARY OF THE INVENTION

Problem to be Solved by the Invention

However, when Abbe's refractometer is used, the critical angle is measured visually in comparison with a scale, and a user not accustomed to the measurement may be unable to read the critical angle accurately, and as a result, precise measurement of refractive index is difficult. Also, when a refractive index measurement apparatus using interference of light is used, it may be necessary to select a good installation site for the apparatus or to refine the structure of the apparatus in order to avoid vibration and to measure the pitch of interference fringes accurately. Thus, there is a problem that the refractive index measurement apparatus may not be easily handled or may become too expensive.

Further, when a refractive index measurement method using diffraction of light is adopted, it is necessary to measure diffraction efficiency many times by varying the temperature of the sample to be measured, or by varying wavelength of light irradiated to the sample to be measured, and therefore, measurement may be complicated.

Thus, it is an object of the present invention to provide a refractive index measurement apparatus and a refractive index measurement method that is simple in construction and that permits refractive index of a sample to be measured in high precision.

Means for Solving the Problem

In accordance with an aspect of the present invention, a refractive index measurement apparatus is provided. The refractive index measurement apparatus includes a light source, a measurement cell including a sample as an object of refractive index measurement and diffracting the light incident from the light source, a detector that detects the amount of diffracted light including at least one diffraction order other than zero order of diffracted light exiting from the measurement cell, and a control unit that uses an equation expressing the relationship between the diffraction efficiency of the at least one diffraction order and refractive index of the sample to determine refractive index of the sample corresponding to the measured value of the amount of the diffracted light of the at least one diffraction order detected by the detector. The measurement cell includes a first transparent substrate and a second transparent substrate disposed so as to be opposed to each other, and a diffraction grating which is formed from a transparent material having a known refractive index and is disposed between the first and the second substrates, and diffracts light from the light source in accordance with the difference of refractive index of the sample and refractive index of the transparent material forming the diffraction grating, wherein the diffraction grating is a binary grating having a plurality of members formed from the transparent material whose width in a first direction parallel to a first surface of the first substrate opposed to the second substrate decreases stepwise as approaching to the second substrate from the first substrate, the plurality of members being arranged periodically at a prescribed pitch along the first direction, and wherein the sample as object of refractive index measurement is filled in the space between the first and the second substrates not occupied by the diffraction grating.

In this refractive index measurement apparatus, preferably, the control unit determines a first calculated value of diffraction efficiency in the at least one diffraction order based on the measured value of the amount of diffracted light at the at least one diffraction order, and determines, from among a plurality of refractive indices presupposed as refractive index of the sample, refractive index that corresponds to the minimum value of error statistics between the first calculated value of the diffraction efficiency in the at least one diffraction order and a second calculated value of diffraction efficiency obtained by inputting the presupposed refractive index to the equation as the refractive index of the sample.

In the refractive index measurement apparatus, the detector preferably detects amount of diffracted light exiting from the measurement cell in plural diffraction orders. The control unit preferably selects, from among the plural diffraction orders, at least two diffraction orders in which the first calculated value of diffraction efficiency is the highest, and identifies the refractive index that corresponds to the minimum value of error statistics between the selected first calculated value of diffraction efficiency and the second calculated value of diffraction efficiency obtained by inputting the presupposed refractive index into the equation as the refractive index of the sample.

It is preferable that the measurement cell further has a first transparent electrode provided on a first surface and a second transparent electrode provided on a second surface of the second substrate opposed to the first substrate, and that the sample is disposed between the first transparent electrode and the second transparent electrode. In this case, the refractive index measurement apparatus preferably further includes an electric power supply circuit that applies a prescribed electric voltage to the sample disposed between the first transparent electrode and the second transparent electrode.

In accordance with another aspect of the present invention, a refractive index measurement method is provided. The refractive index measurement method includes the steps of: directing light from a light source to a measurement cell which has a first and a second substrates formed from transparent material and disposed so as to be opposed to each other, a diffraction grating disposed between the first and the second substrates and formed from transparent material having known refractive index, and a sample as the object of refractive index measurement filled in the space between the first and the second substrates not occupied by the diffraction grating, detecting the amount of diffracted light exiting from the measurement cell in at least one diffraction order of the first or higher order diffracted in accordance with the difference between refractive index of the transparent material and refractive index of the sample, and determining refractive index of the sample corresponding to the measured value of the amount of diffracted light in the at least one diffraction order by using an equation expressing the relationship between the diffraction efficiency in the at least one diffraction order and refractive index of the sample, wherein the diffraction grating is a binary grating having a plurality of members formed from transparent material whose width in the first direction parallel to the first surface of the first substrate decreases stepwise as approaching from the first substrate to the second substrate, the plurality of members being disposed periodically at a prescribed pitch along the first direction.

Effect of the Invention

The refractive index measurement apparatus and the refractive index measurement method according to the present invention have advantageous effect in that it is simple in construction and permits refractive index of a sample to be measured in high precision.

BRIEF DESCRIPTION OF THE DRAWINGS

FIG. 2A is a schematic side sectional view illustrating an example of the measurement cell.

FIG. 2B is a schematic side sectional view illustrating another example of the measurement cell.

DESCRIPTION OF EMBODIMENTS FOR CARRYING OUT THE INVENTION

A refractive index measurement apparatus according to an embodiment will be described in detail with reference to drawings. In this refractive index measurement apparatus, a sample is filled in a measurement cell having a diffraction grating in the inside, and by irradiating light onto the measurement cell to thereby produce diffracted light. The refractive index measurement apparatus measures the amount of diffracted light in at least one diffraction order, and determines refractive index of the sample by comparing the diffraction efficiency obtained from the measured value with calculated value of diffraction efficiency based on an equation expressing the relationship between refractive index of the sample and diffraction efficiency.

Figure 1:
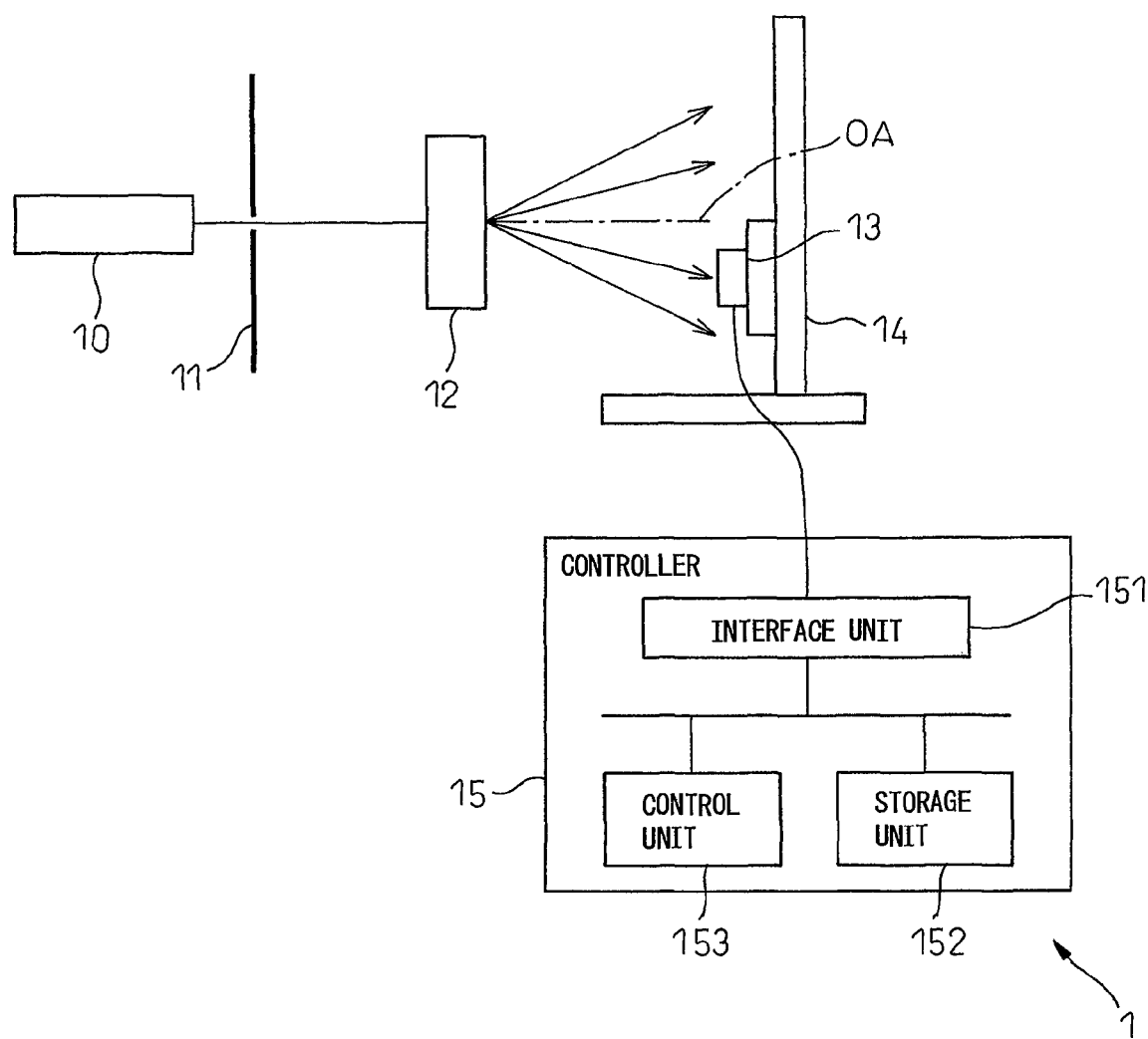
FIG. 1 is a view schematically illustrating the construction of a refractive index measurement apparatus according to an embodiment of the present invention.

FIG. 1 is a view schematically illustrating the construction of the refractive index measurement apparatus according to an embodiment. As illustrated in FIG. 1, the refractive index measurement apparatus 1 includes a light source 10, an aperture stop 11, a measurement cell 12, a detector 13, a movable stage 14, and a controller 15. Among them, the light source 10, the aperture stop 11 and the measurement cell 12 are arranged in a row along the optical axis OA.

The light source 10 is a source emitting light of sufficient intensity that permits diffracted light in at least one diffraction order produced by the measurement cell 12 to be detected by the detector 13, and may be, for example, a semiconductor laser, a gas laser such as a helium-neon laser, or a solid laser such as YAG laser. Alternatively, the light source 10 may be a light emitting diode (LED). In order to simplify calculation of diffraction efficiency by the controller to be described later, the light source 10 is preferably a monochromatic light source emitting monochromatic light of a prescribed wavelength. The prescribed wavelength needs only to be a wavelength to which the detector 13 has sufficient sensitivity, and may be any wavelength included in near infrared to near ultraviolet region. In this embodiment, the light source 10 includes a laser diode emitting light at wavelength of 650 nm.

Light radiated from the light source 10 passes the aperture stop 11 to be irradiated onto the measurement cell 12. The aperture stop 11 has an aperture for forming the spot of light irradiated onto the measurement cell 12 into a prescribed shape, for example, in circular shape. A collimator lens may be disposed between the aperture stop 11 and the measurement cell 12 in order to form the light passing the aperture stop 11 into parallel beam of light. Also, a beam expander may be disposed between the aperture stop 11 and the measurement cell 12 in order to expand the spot diameter of light irradiated to the measurement cell 12.

The measurement cell 12 has a diffraction grating in order to produce diffraction of light in accordance with refractive index of the sample.

FIG. 2A and FIG. 2B are, respectively, schematic side sectional view illustrating examples of the measurement cell 12. The measurement cell 12 has two substrates 121, 122 disposed generally in parallel to each other, and a diffraction grating 123 formed on the substrate 121 between the substrate 121 and the substrate 122. There may be space between the substrate 121 and the substrate 122 where the diffraction grating 123 is not formed. A sample 124 as an object of refractive index measurement is filled in the space between the substrate 121 and the substrate 122 where the diffraction grating 123 is not formed. A sealant (not shown) for preventing leakage of the sample 124 from the measurement cell 12 is provided between the substrate 121 and the substrate 122 so as to surround the diffraction grating 123 and the filled sample 124.

The incident light from the light source 10 enters from outside of the substrate 121 substantially vertically to the outer surface 121a of the substrate 121, and the incident light is diffracted by the diffraction grating 123 to pass through and exit from the substrate 122.

The substrates 121, 122 are, respectively, parallel flat plates formed of material transparent to the incident light from the light source 10, for example, glass or optical plastic material. Material of the substrate 121 may be different from material of the substrate 122. The substrates 121, 122 have thickness of about 0.5 mm to 5 mm, for example. Distance between the substrate 121 and the substrate 122 may be set to a distance that allows the diffraction grating 123 formed between the substrates to have height to give sufficient diffraction efficiency, for example, a few µm to 100 µm.

The diffraction grating 123 diffracts the incident light that enters from the light source 10 into the measurement cell 12. In this embodiment, the diffraction grating 123 is a binary grating having a plurality of step structures 123-1 to 123-n (n is an integer not less than 2) whose width in a first direction parallel to a first surface 121b of the substrate 121 on the side opposed to the second substrate 122 decreasing stepwise when approaching from the first substrate 121 to the second substrate 122, and these step structures are arranged periodically at a specified pitch along the first direction.

Each of the step structures 121-1 to 121-n has one-dimensional structure with the shape varying along with the first direction and not varying along with the direction perpendicular to the first direction. The number of steps of each of the step structures 121-1 to 121-n may be set to any number, for example, from 1 to 8. The larger the number of steps, the higher becomes diffraction efficiency. Thus, when, for example, difference between refractive index of the material forming the step structure and refractive index of the sample 124 is small, and diffraction efficiency obtained in each diffraction order is low, larger number of steps is preferable. Even when the material of the step structure is changed to increase the difference between refractive index of the step structure and refractive index of the sample 124, precision of measurement can be improved by increasing the number of steps.

In the example illustrated in FIG. 2A, the number of steps is 4. On the other hand, in the example illustrated in FIG. 2B, the number of steps is 1. That is, in the example illustrated in FIG. 2B, the step structures 121-1 to 121-n have rectangular cross-sectional shape, respectively.

Height of each step (i.e., length in normal direction to the surface 121b of the substrate 121) is same, and the height of one step is set to about a fraction to a multiple of wavelength of the incident light. For example, when the number of steps is 4, for incident light with wavelength of 650 nm, the height of each step is set to 570 nm. When the number of step is 1, for incident light with wavelength of 650 nm, the height of each step is set to 2280 nm, for example. Alternatively, when the number of step is 8, for incident light with wavelength of 650 nm, the height of each step is set to 285 nm.

The prescribed pitch is set, for example, to a few µm to a few tens of µm in order for the diffraction grating 123 to diffract the incident light.

The diffraction grating 123 may be formed by using, for example, nano-imprint method. Specifically, UV curable resin transparent to the incident light from the light source 10 is, for example, applied to the surface 121b of the substrate 121. A metal die for transferring each step structure is pressed onto the resin. When UV light is irradiated to the resin to harden the resin, each step structure is transferred to the resin and the diffraction grating 123 is formed.

The substrate 122 may be disposed so as to come into contact with the upper end of each step structure of the diffraction grating 123, or it may be disposed so as not to come into contact with the upper end of each step structure. Diffraction of the incident light takes place at the diffraction grating 123, and intensity of the diffracted light is not influenced by positional relation of the substrate 122 and the diffraction grating 123. When the substrate 122 is not in contact with the upper end of each step structure of the diffraction grating 123, a spacer is preferably provided between the substrate 121 and the substrate 122, for example, at each corner of the substrate 121 and the substrate 122, in order to keep separation between the substrate 121 and the substrate 122 at a prescribed distance longer than the height of the step structures.

The sample 124 as an object of refractive index measurement is a material having sufficient transparency, for example, liquid such as solution containing saccharide, gas, or liquid crystal, such that, for the incident light from the light source 10, the amount of diffracted light in at least one diffraction order from the measurement cell 12 filled with the sample 124 can be detected by the detector 13. The sample 124 is filled into the space between the substrate 121 and the substrate 122 not occupied by the diffraction grating formed. Thus, the measurement cell 12 diffracts the incident light in dependence on the difference between refractive index of the member composing the diffraction grating 123 and refraction index of the sample 124.

The detector 13 is disposed on the exit side of the measurement cell 12, and detects the amount of diffracted light produced by the measurement cell 12 in at least one diffraction order. In this embodiment, the detector 13 is disposed so as to be able to detect amount of diffracted light in $\pm 1^{st}$, $\pm 2^{nd}$, $\pm 3^{rd}$, and $0^{th}$ orders. Further, the detector 13 can measure total amount of light exiting from the measurement cell 12.

For this purpose, the detector 13 has a photo-electric conversion device such as a photodiode, CCD or CMOS device, which outputs electrical signal in accordance with the amount of light received. Alternatively, the detector 13 may be an array or a two-dimensional array of such photoelectric devices. The detector 13 is connected to the controller 15 and outputs electrical signal in accordance with the amount of received light to the controller 15.

The detector 13 is mounted on the movable stage 14. The movable stage 14 may be, for example, a so-called XY-stage that can be moved in two mutually orthogonal directions. The detector 13 can be moved along the direction along the optical axis OA or along the direction orthogonal to the optical axis OA in which incident light is diffracted by the measurement cell 12.

When the detector 13 has plural photo-electric conversion devices arranged in one-dimensional or two-dimensional array and can receive diffracted light in plural diffraction orders, the movable stage 14 may be omitted, and the detector 13 may be fixedly mounted on a support member (not shown). In this case, the detector 13 outputs electrical signal in accordance with the amount of received light for each photo-electric conversion device to the controller 15. The controller 15 can determine the amount of light corresponding to each diffraction order based on the electrical signal from the photo-electric conversion device at the relevant position corresponding to the diffraction order.

The controller 15 determines refractive index of the sample filled in the measurement cell 12 based on the amount of diffracted light in at least one diffraction order measured by the detector 13.

For this purpose, the controller 15 has an interface unit 151, a storage unit 152, and a control unit 153.

The interface unit 151 has an interface circuit in accordance with a prescribed communication standard, for example, RS232C, USB, or the like. The interface unit 151 receives electrical signal indicating the measured amount of light from the detector 13, and passes the electrical signal to the control unit 153.

The storage unit 152 has, for example, a semiconductor memory, a magnetic recording medium or an optical recording medium. The storage unit 152 stores various parameters used to determine refractive index of the sample filled in the measurement cell 12. The storage unit 153 may store calculated values of diffraction efficiency in plural diffraction orders, for example, −3 to +3 orders, calculated by the control unit 153 for each of refractive indices included in the presupposed range of refractive index for the sample filled in the measurement cell 12, for example, varied in unit of 0.001 to 0.01, together with the refractive indices.

The control unit 153 has at least one processor and its peripheral circuits. The control unit 153 determines refractive index of the sample filled in the measurement cell 12 by specifying refractive index of the sample corresponding to the measured value of the amount of diffracted light in at least one diffraction order received from the detector 13.

As illustrated in FIG. 2A and FIG. 2B, when the measurement cell 12 has a one-dimensional binary grating, diffraction efficiency of diffracted light in each diffraction order produced by the measurement cell 12 is given by following equation:

$$\eta_m = \left| \sum_{n=0}^{N-1} \exp\left(i2\pi \frac{n\phi}{N}\right) \int_{nP/N}^{(n+1)P/N} \exp\left(-i \frac{2\pi mx}{P}\right) dx \right|^2 \quad (1)$$

where $\eta_m$ represents diffraction efficiency in m-th diffraction order. P is the pitch between adjoining step structures (i.e., pitch of the binary grating), and N is the number of steps of each step structure. $\phi$ is the ratio of optical path difference produced at one step of each step structure to the wavelength of the incident light, expressed in following equation:

$$\phi = D(n_1 - n_2)/\lambda \quad (2)$$

where $n_1$, $n_2$ are refractive index of the material forming the step structure and refractive index of the sample filled in the measurement cell 12, respectively, and D is the height of one step of the step structure. $\lambda$ represents the wavelength of the incident light.

As is evident from equations (1) and (2), diffraction efficiency is determined in accordance with the difference between refractive index $n_1$ of the material forming the step structure and refractive index $n_2$ of the sample filled in the measurement cell 12. Parameters used to determine diffraction efficiency $\eta_m$ are all known except the refractive index $n_2$ of the sample 124. Thus, the control unit 153 can determine refractive index of the sample by identifying refractive index of the sample that gives diffraction efficiency of the sample from the equations (1) and (2) that matches with the diffraction efficiency obtained from measured value of the amount of diffracted light.

Diffraction efficiency in a prescribed diffraction order is defined as the ratio of the amount of diffracted light $I_D$ in the diffraction order to the amount of light $I_{in}$ incident on the measurement cell 12 (i.e., $I_D/I_{in}$). Therefore, the control unit 153 determines, for example, the ratio of the amount of diffracted light in at least one diffraction order from measurement cell 12 to the total amount of light exiting from the measurement cell 12 as a first calculated value of diffraction efficiency in the diffraction order.

The control unit 153 may determine diffraction efficiency in each diffraction order by detecting the total amount of light transmitted by the portion not containing the diffraction grating in the measurement cell 12 with the detector 13 and by dividing the amount of diffracted light in each diffraction order by this total amount of light. In more strict measurement of diffraction efficiency, transmittance T of the sample (i.e., the amount of transmitted light/the amount of incident light) is measured in advance in the portion of the measured sample having no diffraction structure formed. The value obtained by dividing the measured diffraction efficiency by the transmittance T is nearer to the true diffraction efficiency. In order to measure transmittance, a region to which no diffraction structure is added is preferably provided in the measurement cell 12. Size of this region preferably corresponds to the diameter of the laser beam incident on the measurement cell 12, for example, size covering a circular region having diameter of 2 mm to 7 mm.

On the other hand, the control unit 153 determines a second calculated value of diffraction efficiency by inputting value of refractive index presupposed as refractive index of the sample 124 and known values of other parameters into the equations (1) and (2). If the second calculated value of diffraction efficiency in each diffraction order corresponding to the presupposed refractive index is stored in the storage unit 152, the control unit 153 may read out this second calculated value of diffraction efficiency from the storage unit 152, and may utilize it. The control unit 153 can thereby reduce the calculation load at the time of refractive index measurement, and can identify the refractive index $n_2$ which gives the second calculated value of diffraction efficiency that best matches with the first calculated value of diffraction efficiency as the refractive index of the sample actually measured.

Preferably, the control unit 153 selects a prescribed number of diffraction orders in order of higher diffraction efficiency, from among plural diffraction orders in which diffraction efficiency has been measured, and identifies the refractive index $n_2$ which corresponds to the minimum value of error statistics between the first calculated value of diffraction efficiency and the second calculated value of diffraction efficiency as the refractive index of the sample actually measured. The prescribed number is an integer not less than 1 and not more than total number of diffraction order in which the amount of diffracted light has been measured. This prescribed number is preferably set to an integer not less than 2 in order to reduce the influence of measurement error due to noise at the time of measurement of the amount of diffracted light and to measure refractive index of the sample accurately.

Zero order is not included as diffraction orders used to calculate the error statistic. This is because zero order corresponds to light transmitted without diffraction. The error statistic may be, for example, the total sum of squares of error between the first calculated value of diffraction efficiency and the second calculated value of diffraction efficiency in each diffraction order, or the total sum or mean of the absolute value of error between the first calculated value of diffraction efficiency and the second calculated value of diffraction efficiency in each diffraction order.

The control unit 153 can measure refractive index of the sample in high precision by obtaining the minimum value of error statistic of difference between the first calculated value and the second calculated value of diffraction efficiency in at least one diffraction order and by determining refractive index corresponding to the minimum value.

Figure 3:
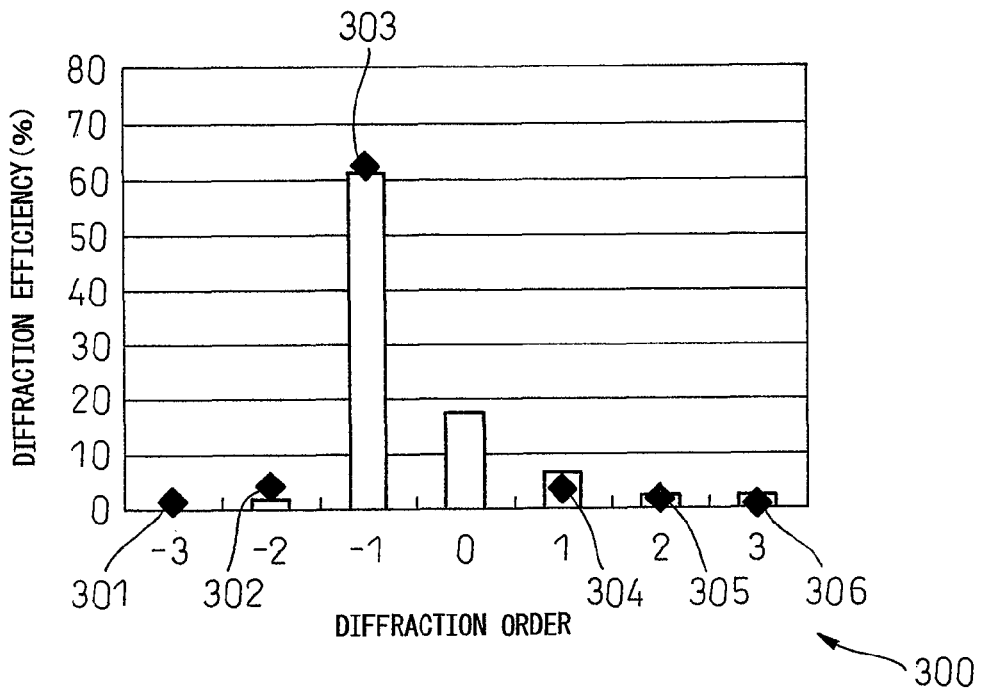
FIG. 3 is a graph depicting an example of experimental result illustrating the calculated value of diffraction efficiency based on equations expressing diffraction efficiency that gives the least error statistic of error from the value of diffraction efficiency obtained from the measured value of amount of diffracted light for a sample having refractive index of 1.69.

FIG. 3 is a graph illustrating an example of experimental result representing second calculated value of diffraction efficiency with the minimum error statistic in comparison with the first calculated value of diffraction efficiency obtained from the amount of diffracted light detected by the detector 13 for a sample with refractive index of 1.69.

In the graph 300 illustrated in FIG. 3, horizontal axis represents diffraction order and vertical axis represents diffraction efficiency (%). Each bar graph shows the first calculated value of diffraction efficiency obtained from the amount of diffracted light detected by the detector 13. On the other hand, each point 301 to 306 shows, for two diffraction orders in order of larger first calculated value of diffraction efficiency (here, $-1^{st}$ and $1^{st}$ orders), the second calculated values of diffraction efficiency with refractive index of the sample giving the least error statistic. As illustrated in FIG. 3, in each diffraction order within the range of $\pm 3^{rd}$ orders, good coincidence between the first calculated value and the second calculated value has been obtained. Thus, it can be seen that the refractive index used to calculate the second calculated value substantially matches with the refractive index of the sample filled in the measurement cell.

Figure 4:
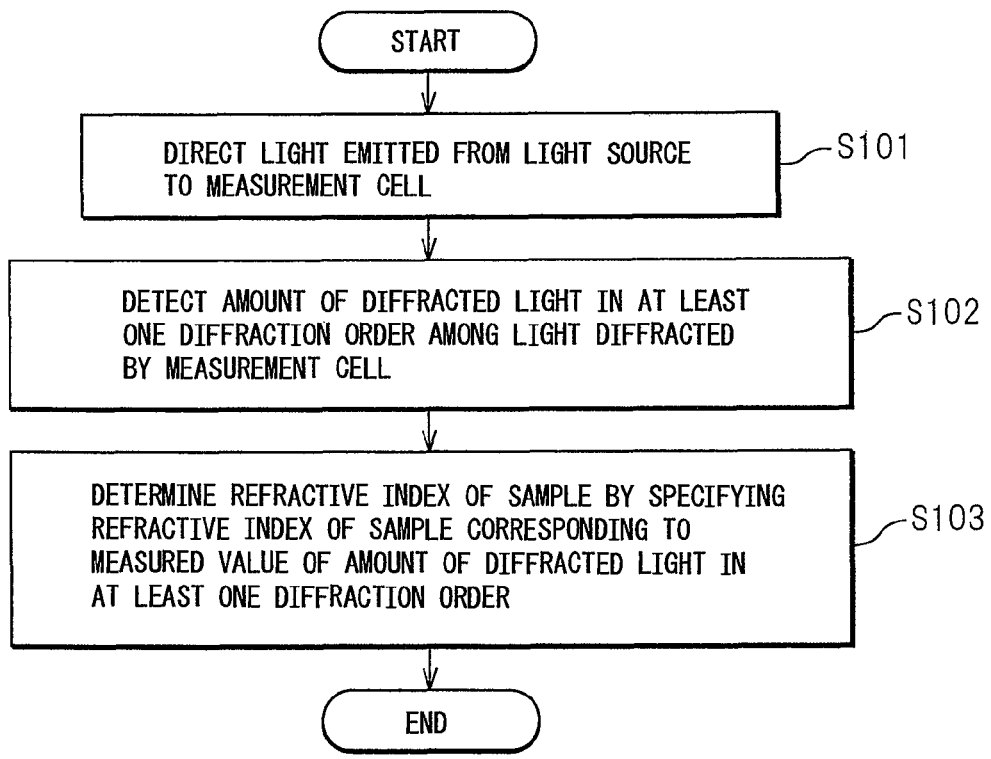
FIG. 4 is a flow chart of the refractive index measurement method.

FIG. 4 is a flow chart of the refractive measurement method carried out by the refractive index measurement apparatus 1.

Light emitted by the light source 10 passes through the aperture stop 11 and is directed to the measurement cell 12 (step S101). The measurement cell 12 diffracts the incident light. The detector 13 detects the amount of diffracted light in at least one diffraction order exiting from the measurement cell 12 (step S102). The detector 13 outputs electrical signal corresponding to the amount of diffracted light to the controller 15.

The control unit 153 of the controller 15 determines refractive index of the sample by specifying the refractive index of the sample corresponding to the measured value of the amount of diffracted light in at least one diffraction order (step S103). Specifically, as described above, the control unit 153 identifies, from among a plurality of refractive indices presupposed as refractive index of the sample, refractive index that corresponds to the minimum value of error statistics between the second calculated value of diffraction efficiency in each diffraction order and the first calculated value obtained from the measured value of the amount of diffracted light in the corresponding diffraction order as the refractive index of the sample. The control unit 153 of the controller 15 stores the measurement result of the refractive index of the sample in the storage unit 152. Alternatively, the control unit 153 displays the measurement result of the refractive index of the sample on a display device (not shown).

As has been described above, The refractive index measurement apparatus according to an embodiment of the present invention measures the refractive index of the sample by detecting the amount of diffracted light in at least one diffraction order diffracted in accordance with the refractive index of the sample. Diffraction efficiency in each diffraction order of diffracted light is not affected by the vibration applied to this refractive index measurement apparatus. Therefore, the refractive index measurement apparatus does not require a base isolation structure and can be constructed simply. Further, when preparing the measurement cell, the sample needs only to be filled in the measurement cell, and precise processing of the sample is not required. Since the separation between substrates of the measurement cell does not influence diffraction efficiency, preparation of the measurement cell can be simplified.

Further, if the diffraction grating in the measurement cell is formed precisely, the diffraction efficiency by the diffraction grating having the known one-dimensional periodic structure can be obtained accurately by calculation equation from diffraction theory, and error between the value of diffraction efficiency obtained from the calculation equation and the value of diffraction efficiency determined from the measured value of the amount of diffracted light is small. Therefore, this refractive index measurement apparatus can measure refraction index of the sample accurately. Since the size of the measurement cell for producing diffraction may be small, quantity of the sample filled in the measurement cell may also be small. Further, since this refractive index measurement apparatus can determine refractive index of the sample using measured value of diffraction efficiency in diffraction orders other than zero order obtained in one-time irradiation of light to the measurement cell, procedure of refraction index measurement is simplified.

The present invention is not limited to the embodiment described above. For example, according to another embodiment, the measurement cell may have transparent electrodes provided on the surface of the two substrates in order to be able to measure refractive index of a sample in which refractive index varies in accordance with applied electric voltage, for example, refractive index of a liquid crystal, for each electric voltage applied to the sample.

Figure 5:
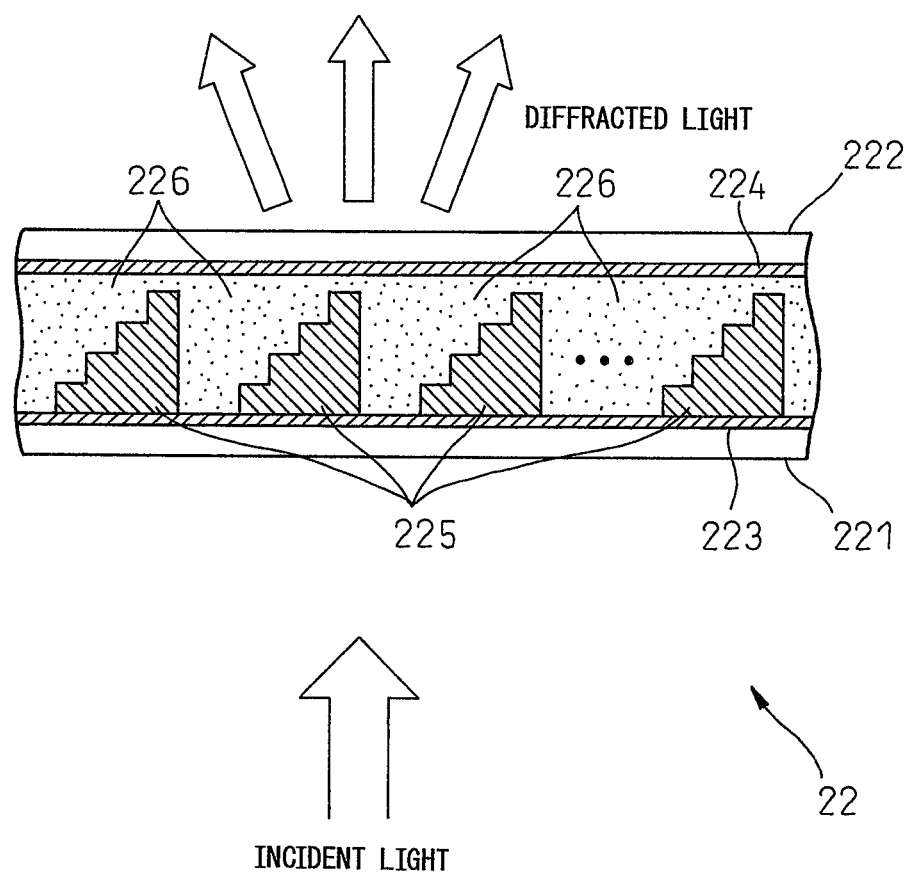
FIG. 5 is a schematic side sectional view illustrating a measurement cell according to another embodiment.

FIG. 5 is a schematic side sectional view illustrating a measurement cell having transparent electrodes. The measurement cell 22 has substrates 221, 222 disposed substantially in parallel to each other, transparent electrodes 223, 224 respectively provided on inner surface of the substrates 221 and 222, and a diffraction grating 225 formed on the transparent electrode 223 between the substrates 221 and 222. A sample 226 as an object of refractive index measurement is filled into space between the transparent electrodes not occupied by the diffraction grating 225. The transparent electrodes 223, 224 may be formed, for example, from material called ITO, i.e., indium oxide added with tin oxide. The diffraction grating 225 may have similar construction as the diffraction grating 123 illustrated in FIG. 2A or FIG. 2B.

Further, when the sample 226 contains liquid crystal molecules, an aligning film for aligning the liquid crystal molecules in a prescribed direction may be provided on the surface of the transparent electrodes 223 and 224.

Figure 6:
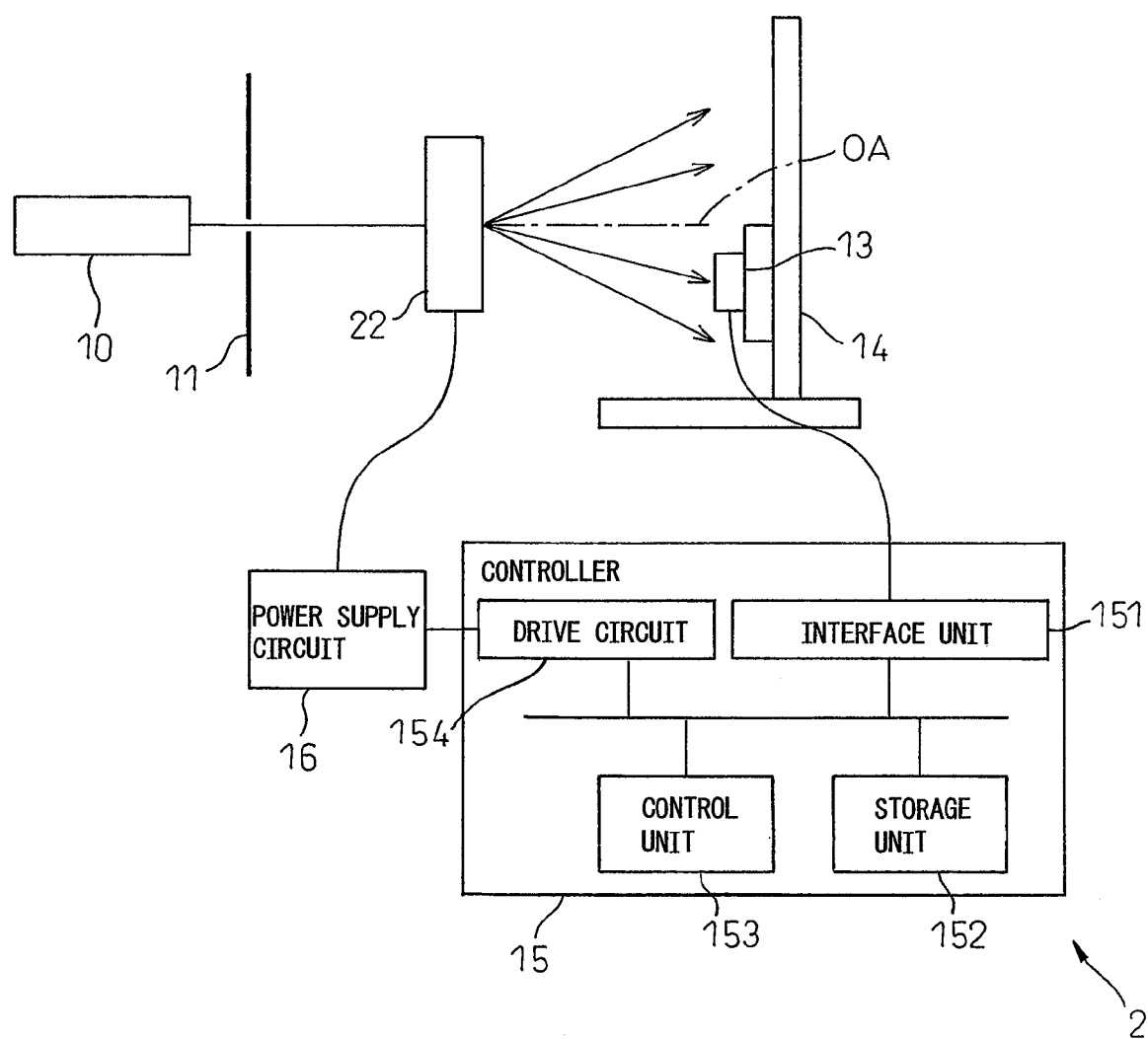
FIG. 6 is a view schematically illustrating a refractive index measurement apparatus which uses the measurement cell illustrated in FIG. 5.

FIG. 6 is a view schematically illustrating the construction of a refractive index measurement apparatus according to another embodiment of the present invention that utilizes the measurement cell illustrated in FIG. 5. The refractive index measurement apparatus 2 includes a light source 10, an aperture stop 11, a measurement cell 22, a detector 13, a movable stage 14, a controller 15 and an electric power supply circuit 16. The controller 15 has an interface unit 151, a storage unit 152, a control unit 153 and a drive circuit 154 for driving the power supply circuit 16. In FIG. 6, each part of the refractive index measurement apparatus 2 is denoted by same reference numeral as the reference numeral used to denote corresponding part of the refractive index measurement apparatus 1 illustrated in FIG. 1.

In what follows, only those points that differ from the refractive index measurement apparatus 1 will be described.

The control unit 153 of the controller 15 controls the drive circuit 154 via a user-interface (not shown) such as a keyboard or a mouse such that a designated electric voltage is applied between the transparent electrodes 223 and 224 of the measurement cell 22. For example, suppose a case where liquid crystal molecules, are filled as the sample in the measurement cell 22, and are aligned such that long axis of the liquid crystal molecule is orthogonal to the optical axis OA and is parallel to the polarization plane of the incident light. In such case, the designated electric voltage is set, for example, to an electric voltage sufficient to rotate the long axis of the liquid crystal molecule so as to form a prescribed angle with the optical axis OA. The drive circuit 154 outputs a control signal corresponding to the designated electric voltage to the power supply circuit 16.

The power supply circuit 16 generates a drive electric voltage in accordance with the control signal from the controller 15, and the drive electric voltage is applied between the transparent electrodes 223 and 224 of the measurement cell 22.

The drive electric voltage applied between the transparent electrodes 223 and 224 may be, for example, AC voltage with pulse height modulation (PHM) or pulse width modulation (PWM).

With the prescribed electric voltage applied between the transparent electrodes 223 and 224, the refractive index measurement apparatus 2 can measure the refractive index of the sample 226 having the prescribed electric voltage applied thereto, by irradiating the measurement cell 25 with the light from the light source 10 and measuring the amount of diffracted light in at least one diffraction order with the detector 13. Thus, by adjusting the electric voltage applied between the transparent electrodes 223 and 224, the refractive index measurement apparatus 2 can measure the refractive index of the sample 226 with various electric voltage applied thereto.

The diffraction grating of the measurement cell used in any of the above-described embodiments may have various structures that permit diffraction efficiency of the diffraction to be produced by the diffraction grating. For example, the diffraction grating of the measurement cell may be a blazed grating having periodically arranged saw tooth structure. Alternatively, the diffraction grating may have periodic structure formed in a concentric form.

The diffraction grating may be formed on the substrate on exiting side, i.e., on the second substrate in above-described embodiments.

As has been described above, those skilled in the art can make various modifications within the scope of the present invention in accordance with embodiments.

DESCRIPTION OF REFERENCE NUMERALS 1, 2 refractive index measurement apparatus
10 light source
11 aperture stop
12, 22 measurement cell
13 detector
14 movable stage
15 controller
16 power supply circuit
121, 122, 221, 222 transparent substrate
123, 225 diffraction grating
123-1 to 123-$n$ step structure
124, 226 sample
223, 224 transparent electrode
151 interface unit
152 storage unit
153 control unit
154 drive circuit

The invention claimed is:

1. A refractive index measurement apparatus comprising:
a light source;
a measurement cell including a sample as an object of refractive index measurement, and diffracting light incident from the light source;
a detector that detects the amount of diffracted light exiting from the measurement cell in at least one diffraction order including a diffraction order other than zero order; and
a control unit that determines refractive index of the sample corresponding to measured value of the amount of diffracted light in the diffraction order other than zero order among the at least one diffraction order detected by the detector using an equation expressing the relationship between diffraction efficiency in the diffraction order other than zero order among the at least one diffraction order and refractive index of the sample;
wherein the measurement cell includes:
a first transparent substrate and a second transparent substrate disposed so as to be opposed to each other so that a space in which the sample is filled is included between the first substrate and the second substrate; and
a diffraction grating that is formed from transparent material having known refractive index, is disposed between the first substrate and the second substrate, and lies adjacent to the space, and diffracts light from the light source in accordance with difference between refractive index of the sample and refractive index of the transparent material;
wherein the diffraction grating is a binary grating having a plurality of members formed from the transparent material whose width in a first direction parallel to a first surface of the first substrate opposed to the second substrate decreases stepwise as approaching from the first substrate to the second substrate, the plurality of members being periodically arranged at a prescribed pitch along the first direction;
wherein the control unit obtains a first calculated value of diffraction efficiency in the diffraction order other than zero order among the at least one diffraction order based on measured value of the amount of diffracted light in the diffraction order other than zero order among the at least one diffraction order, and identifies, from among plural refractive indices presupposed as refractive index of the sample, refractive index which corresponds to a minimum value of error statistics between the first calculated value of diffraction efficiency and a second calculated value of diffraction efficiency obtained by inputting the presupposed refractive index into the equation expressing the relationship as refractive index of the sample.

2. The refractive index measurement apparatus according to claim 1, wherein the detector detects the amount of diffracted light in plural diffraction orders of diffracted light exiting from the measurement cell, and wherein the control unit selects at least two diffraction orders in higher order of the first calculated value of diffraction efficiency from the plural diffraction orders, and identifies refractive index which corresponds to the minimum value of error statistics between the first calculated value of diffraction efficiency and the second calculated value of diffraction efficiency obtained by inputting the presupposed refractive index to the equation expressing the relationship as refractive index of the sample.

3. The refractive index measurement apparatus according to claim 1, wherein the measurement cell further includes a first transparent electrode provided on the first surface and a second transparent electrode provided on a second surface of the second substrate opposed to the first substrate, the sample being disposed between the first transparent electrode and the second transparent electrode, and wherein the apparatus further comprises a power supply circuit that applies a prescribed electric voltage to the sample disposed between the first transparent electrode and the second transparent electrode.

4. A refractive index measurement method comprising the steps of:
  directing light from a light source to a measurement cell which includes a sample as an object of refractive index measurement, a first transparent substrate and a second transparent substrate disposed so as to be opposed to each other so that a space in which the sample is filled is included between the first substrate and the second substrate, and a diffraction grating that is formed from transparent material of known refractive index, is disposed between the first substrate and the second substrate and lies adjacent to the space;
  detecting the amount of diffracted light in at least one diffraction order including a diffraction order other than zero order of diffracted light exiting from the measurement cell and diffracted in accordance with difference of refractive index of the transparent material and refractive index of the sample;
  determining refractive index of the sample corresponding to measured value of the amount of diffracted light in the diffraction order other than zero order among the at least one diffraction order by using an equation expressing the relationship between diffraction efficiency in the diffraction order other than zero order among the at least one diffraction order and refractive index of the sample;
  wherein the diffraction grating is a binary grating having a plurality of members formed from the transparent material whose width in a first direction parallel to a first surface of the first substrate opposed to the second substrate decreases stepwise as approaching from the first substrate to the second substrate, the plurality of members being periodically arranged at a prescribed pitch along the first direction, and
  the determining refractive index of the sample including:
  obtaining a first calculated value of diffraction efficiency in the diffraction order other than zero order among the at least one diffraction order based on the measured value of the amount of diffracted light in the diffraction order other than zero order among the at least one diffraction order, and
  identifying, from among plural refractive indices presupposed as refractive index of the sample, refractive index which corresponds to a minimum value of error statistics between the first calculated value of diffraction efficiency and a second calculated value of diffraction efficiency obtained by inputting a presupposed refractive index into the equation expressing the relationship as refractive index of the sample.

* * * * *